(12) United States Patent
Ha et al.

(10) Patent No.: US 8,895,412 B2
(45) Date of Patent: Nov. 25, 2014

(54) NANO-STRUCTURE MANUFACTURING METHOD USING SACRIFICIAL ETCHING MASK

(71) Applicant: Korea Institute of Science and Technology, Seoul (KR)

(72) Inventors: Seung Kyu Ha, Seoul (KR); Su Youn Kim, Seoul (KR); Il Ki Han, Seoul (KR); Jin Dong Song, Seoul (KR); Won Jun Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 81 days.

(21) Appl. No.: 13/668,526

(22) Filed: Nov. 5, 2012

(65) Prior Publication Data

US 2014/0030872 A1    Jan. 30, 2014

(30) Foreign Application Priority Data

Jul. 26, 2012    (KR) .................... 10-2012-0081674

(51) Int. Cl.

| H01L 21/20 | (2006.01) |
|---|---|
| H01L 21/02 | (2006.01) |
| H01L 29/12 | (2006.01) |
| B82Y 10/00 | (2011.01) |
| H01L 29/06 | (2006.01) |
| G01N 21/00 | (2006.01) |
| H01L 29/76 | (2006.01) |
| B82Y 40/00 | (2011.01) |

(52) U.S. Cl.
CPC .... H01L 21/02104 (2013.01); H01L 21/02601 (2013.01); H01L 21/02546 (2013.01); H01L 29/127 (2013.01); B82Y 10/00 (2013.01); H01L 29/0665 (2013.01); H01L 21/02631 (2013.01); G01N 21/00 (2013.01); H01L 29/7613 (2013.01); B82Y 40/00 (2013.01); Y10S 977/84 (2013.01)
USPC .......................................... 438/478; 977/840

(58) Field of Classification Search
CPC ..................................................... H01L 21/02
USPC .......................................... 438/478; 977/840
See application file for complete search history.

(56) References Cited

U.S. PATENT DOCUMENTS

| 2008/0009121 A1* | 1/2008 | Wei .............................. 438/406 |
| 2010/0155786 A1* | 6/2010 | Heald et al. .................... 257/213 |
| 2013/0284257 A1* | 10/2013 | Gilchrist et al. .............. 136/256 |

FOREIGN PATENT DOCUMENTS

| JP | 2000-315653 A | 11/2000 |
| JP | 2012-124500 A | 6/2012 |

(Continued)

OTHER PUBLICATIONS

Young-Jun Yu, Wonho Jhe, and Yasuhiko Arakawa; 'High-resolution near-field spectroscopy of InAs single quantum dots at 70 K', Applied Physics Letters 83, 3024 (2003); doi: 10.1063/1.1618949.*

(Continued)

*Primary Examiner* — Jarrett Stark
*Assistant Examiner* — Mohammad M Hoque
(74) *Attorney, Agent, or Firm* — Ladas & Parry LLP

(57) ABSTRACT

Disclosed is a nano-structure manufacturing method which includes: forming a first semiconductor composite layer, a semiconductor quantum structure layer, a second semiconductor composite layer, and a semiconductor quantum dot layer on a substrate in order; thermally treating the semiconductor quantum dot layer so that quantum dots of the semiconductor quantum dot layer are aggregated; and performing an etching process by using the aggregated quantum dots as a mask.

11 Claims, 5 Drawing Sheets

(56) References Cited

FOREIGN PATENT DOCUMENTS

| KR | 100301116 | B1 | 6/2001 |
|---|---|---|---|
| KR | 100622819 | B1 | 9/2006 |
| KR | 1020070063731 | A | 6/2007 |
| KR | 100867499 | B1 | 10/2008 |

OTHER PUBLICATIONS

Young et al.; Near-field photoluminescence study of InAs/AlGaAs quantum-dot-based nanoclusters: band filling effect; Center for Near-field Atom-photon Technology and School of Physics, Seoul National University, Seoul 151-742, Korea.*

A. Dousse, et al; "Controlled Light-Matter Coupling for a Single Quantum Dot Embedded in a Pillar Microcavity Using Far-Field Optical Lithography", Physical Review Letters, 101, week ending Dec. 31, 2008; pp. 267404-1-267404-4.

Takaaki Mano, et al; "Formation of InGaAs Quantum Disks Using Droplet Lithography", Japanese Journal of Applied Physics, vol. 46, No. 30, pp. L736-L738; published online Jul. 27, 2007.

X. Qian, et al; "Uniform InGaAs quantum dot arrays fabricated using nanosphere lithography", Appl. Phys. Lett. 93; published online Dec. 11, 2008; pp. 231907-1-231907-3.

Young-Jun Yu, et al; "Near-Field Photoluminescence Study of InAs/AlGaAs Quantum-Dot-Based Nanoclusters", Japanese Journal of Applied Physics, vol. 45, No. 2A, published online Feb. 8, 2006, pp. 656-659.

* cited by examiner

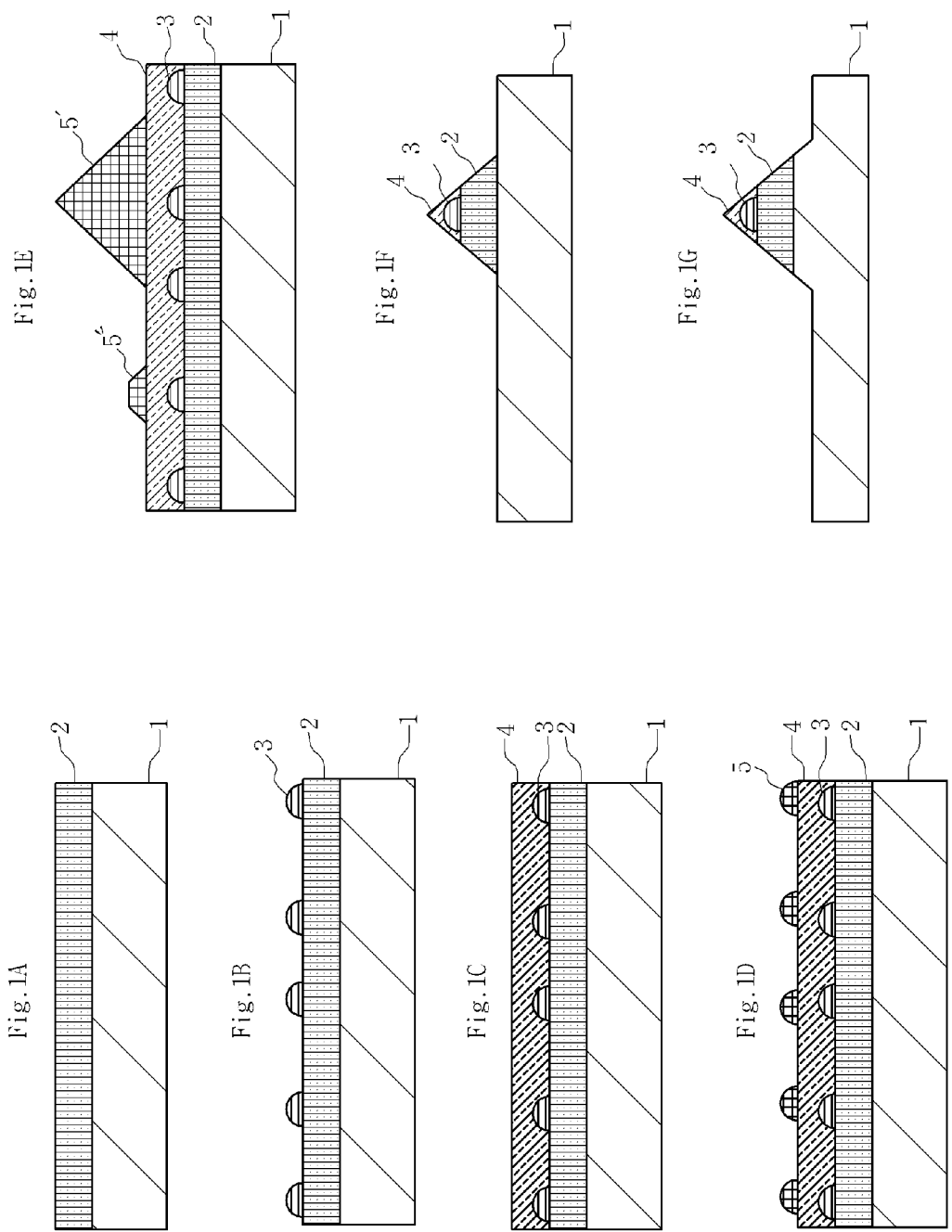

NANO-STRUCTURE MANUFACTURING METHOD USING SACRIFICIAL ETCHING MASK

CROSS-REFERENCE TO RELATED APPLICATION

This application claims priority to Korean Patent Application No. 10-2012-0081674, filed on Jul. 26, 2012, and all the benefits accruing therefrom under 35 U.S.C. §119, the contents of which in its entirety are herein incorporated by reference.

BACKGROUND

1. Field

The present disclosure relates to a method for manufacturing nano-structures disposed to decrease surface density of semiconductor quantum structures which have quantum confinement effect like semiconductor quantum dots, and more particularly, to a nano-structure manufacturing method using a sacrificial etching mask.

2. Description of the Related Art

The semiconductor material shows features different from its bulk structure when quantum confinement effect is applied by forming nano-structures like a quantum well, a quantum wire, or a quantum dot. It is because state and distribution of the electrons in the semiconductor material structure change according to the degree of quantum confinement, and the features are physically and chemically distinguished from the state of bulk; for example, the change of band gap, the reinforcement of electron confinement, the formation of quantized internal energy levels, or the like.

Among them, compound semiconductor quantum dots have been recently studied to develop the laser which is insensitive to temperature, the photon detector which is sensitive to long-wavelength photons, the single photon emitting source which may be applied to the quantum encoded communication and the quantum calculation, or the like, by means of three-dimensional electron confinement.

In order to study such a semiconductor quantum dot, individual features should be revealed through measurement of an isolated single quantum dot. However, optical devices conventionally used for measuring features of a single quantum dot do not have enough resolution to distinguish signals from the adjacent quantum dots grown with a surface density higher than 1 $\mu m^{-2}$. However, in the conventional quantum dot growth technique, the quantum dots are irregularly grown to have a surface density of 1 to 10 $\mu m^{-2}$ in a statistical aspect even though the low density growth technique is applied.

In other words, in the above technique, generally, quantum dot specimens are grown several times so that a quantum dot specimen grown with a lower density is selected and used, or the entire surface of a quantum dot specimen is investigated so that a portion grown with a lower density is selected and used. Therefore, there is a limit in consistent reproduction of quantum dot specimens of a low surface density.

Therefore, as a method for additionally decreasing surface density of quantum dots in a specimen, an array of nano-structures may be manufactured to have a surface density which is lower than the surface density of the quantum dots in the specimen. Since the nano-structures are formed by etching layers including the quantum dots, quantum dots exist only inside the nano-structures and the surface density of the quantum dots are reduced. Representatively, there are methods for manufacturing nano-structures such as mesa or micropillar where each nano-structure has a diameter less than 1 μm and the surface density of the nano-structures is less than 1 $\mu m^{-2}$.

However, the mesa or micropillar manufacturing method requires an additional process using the electron-beam (E-beam) lithography technique after the growth of a compound semiconductor specimen in order to form the nano-structures.

In the conventional E-beam lithography, negative E-beam resist (ER) is spin-coated on a grown specimen and then E-beam is irradiated to designate size and position of the nano-structures. As a result, the E-beam resist remains only at the E-beam irradiated points, and the remaining E-beam resist is utilized as a mask to form desired nano-structures by etching.

SUMMARY

The conventional mesa or micropillar manufacturing method has several disadvantages such as the complicated processing steps, the contamination of a compound semiconductor specimen due to coating of E-beam resist, the damage of a specimen due to electron collision caused by E-beam irradiation. Moreover, expensive operation fee and slow operation speed of an E-beam lithography system severely limit manufacturing nano-structures on a large area of a specimen.

Therefore, an inexpensive and simplified nano-structure manufacturing method which may prevent a specimen from being contaminated or damaged without using an E-beam lithography system is demanded.

In one aspect, there is provided a nano-structure manufacturing method, which includes: forming a first semiconductor composite layer, a semiconductor quantum structure layer, a second semiconductor composite layer, and a semiconductor quantum dot layer on a substrate in order; thermally treating the semiconductor quantum dot layer so that quantum dots of the semiconductor quantum dot layer are aggregated; and performing an etching process by using the aggregated quantum dots as a mask. In addition, the semiconductor quantum structure layer may include at least one of a quantum dot, a quantum wire, a quantum well, a quantum dash, or a quantum molecule. In addition, the quantum dots of the semiconductor quantum structure layer and the quantum dots of the semiconductor quantum dot layer may be made of the same semiconductor material. In addition, the first semiconductor composite layer, the semiconductor quantum structure layer, the second semiconductor composite layer, and the semiconductor quantum dot layer may be made of materials with the same etching rate. In addition, the quantum dots of the semiconductor quantum structure layer and the quantum dots of the semiconductor quantum dot layer may be formed by means of droplet epitaxy. In addition, the thermal treatment of the semiconductor quantum dot layer may be performed by rapid thermal annealing at 500° C. to 1200° C. for 30 seconds to 10 minutes. In addition, the thermal treatment of the semiconductor quantum dot layer may include: blocking both top and bottom surfaces of a specimen by using two impurity-undoped semi insulating (SI)-GaAs substrates; and performing thermal treatment at 750° C. for 4 minutes within nitrogen atmosphere. In addition, performing of an etching process by using the aggregated quantum dots as a mask, the region from the bottom of the first semiconductor composite layer to the top of the second semiconductor composite layer may be formed in the shape of the aggregated quantum dots of the semiconductor quantum dot layer. In addition, the quantum dots of the semiconductor quantum structure layer and the semiconductor quantum dot layer may be made of GaAs. In addition, the first semiconductor composite layer and the second semiconductor composite layer may be made of AlGaAs. In addition, the above-mentioned quantum dots made of GaAs may be formed by means of droplet epitaxy.

According to an aspect of the present disclosure, it is possible to prevent a specimen from being contaminated by E-beam resist or damaged by E-beam, and also nano-structures may be rapidly manufactured on a large area of a specimen through reduced number of processing steps.

BRIEF DESCRIPTION OF THE DRAWINGS

The above and other aspects, features and advantages of the disclosed exemplary embodiments will be more apparent from the following detailed description taken in conjunction with the accompanying drawings.

FIG. 1A-1D show a semiconductor structure presenting a cross-sectional structure grown by using the MBE equipment.

FIG. 1E-1G show a semiconductor structure presenting a cross-sectional structure etched.

DETAILED DESCRIPTION

Figure 2A:
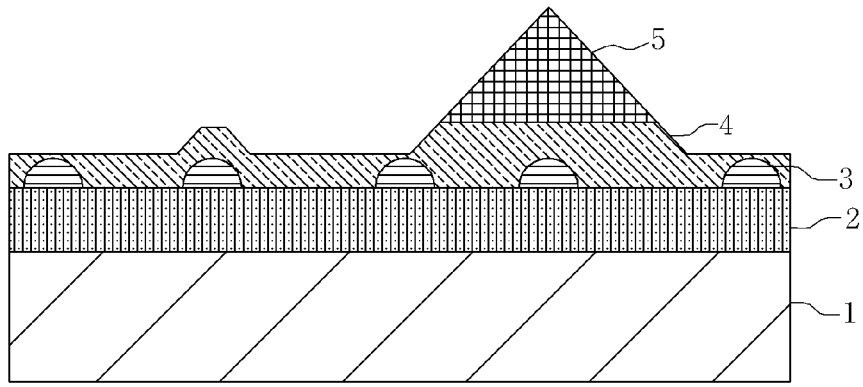
FIG. 2A-2D show a semiconductor structure presenting a cross-sectional structure etched according to an embodiment of the present disclosure.
Figure 2B:
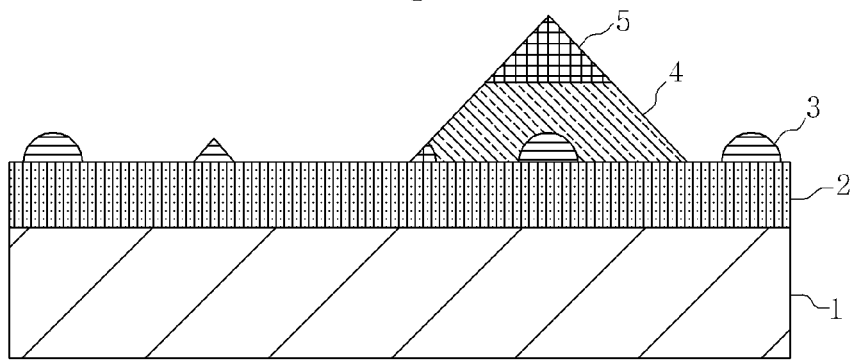
Figure 2C:
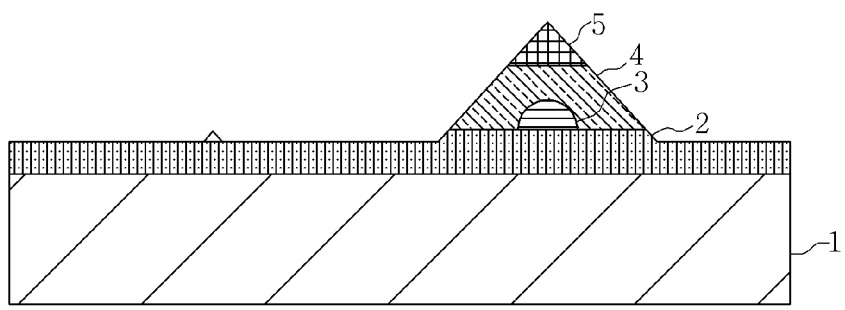

Hereinafter, embodiments of the present disclosure will be described in detail with reference to the accompanying drawings.

FIG. 1A-B show a nano-structure manufacturing method according to an embodiment of the present disclosure.

As shown in FIG. 1A, a first semiconductor composite layer 2 may be formed on a semiconductor substrate 1. In addition, as shown in FIG. 1B, a semiconductor quantum structure layer 3 may be formed on the first semiconductor composite layer 2. In addition, as shown in FIG. 1C, a second semiconductor composite layer 4 may be formed on the semiconductor quantum structure layer 3.

The semiconductor quantum structure layer 3 may be formed with the same material and structure as, or different material and structure from, the semiconductor quantum dot layer which operates as a sacrificial mask. In addition, the semiconductor quantum structure layer may include a quantum dot as well as various quantum structures such as a quantum wire, a quantum well, a quantum dash, and a quantum molecule in combinations or any one of them.

In an embodiment, a semiconductor quantum structure layer may include quantum dot including various materials (e.g. GaAs quantum dot, InAs quantum dot, InGaAs quantum dot, etc.).

In addition, as shown in FIG. 1D, a semiconductor quantum dot layer 5 may be formed on the second semiconductor composite layer 4. The uppermost layer (semiconductor quantum dot layer 5) may be thermally treated to aggregate the quantum dots of the uppermost layer. In addition, the aggregated semiconductor quantum dots (the aggregated material, 5') may be used as a mask to perform an etching process.

The aggregated material 5' is entirely etched and removed, and the region from the bottom of the first semiconductor composite layer 2 to the top of the second semiconductor composite layer 4 may be etched to have the same shape as the aggregated material 5'. In addition, the etching may be performed until the substrate is partially removed. Through this process, nano-structures including a single quantum dot in each of them may be formed.

Generally, a semiconductor material layer designed to be removed after etching in a semiconductor process is called a sacrificial layer so that the aggregated semiconductor materials used as a mask in etching and then removed as described above may be called a sacrificial mask.

Figure 2D:
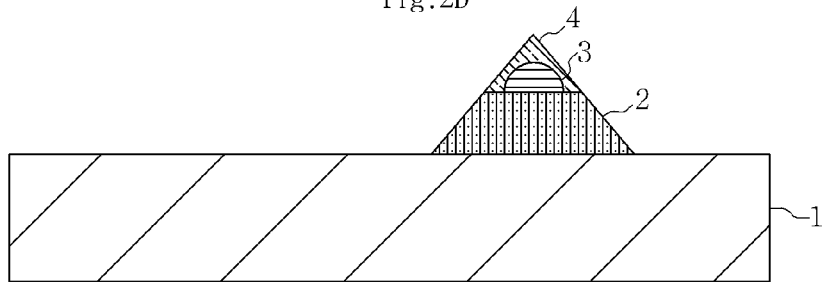

Referring to FIG. 2A-D, a specific etching process of FIG. 1E to FIG. 1F according to an embodiment of the present disclosure is shown in order. In FIG. 1E, A relatively large aggregated material 5' protects the region from the first semiconductor composite layer to the top of the second semiconductor composite layer from etching and be a large aggregated material 5 in FIG. 2A so that a quantum dot positioned below the large aggregated material is maintained among the quantum dots of the semiconductor quantum structure layer (FIG. 2D, wherein FIG. 2D is consistent with FIG. 1F) (a small aggregated material 5" does not serve as a mask eventually). In FIG. 2A, when etching process is performed, a large aggregated material 5 is removed slightly (referring to FIG. 2B). And then a part of the semiconductor quantum structure layer 3, the second semiconductor composite layer 4, and the large aggregated material 5 are removed by continued etching process (referring to FIG. 2C). And the all large aggregated material 5 is removed by continued etching process (referring to FIG. 2D).

As a result, a nano-structure including a single quantum dot may be formed within the region from the bottom of the first semiconductor composite layer to the top of the second semiconductor composite layer.

The semiconductor substrate 1 may be GaAs, and the first semiconductor composite layer 2 and the second semiconductor composite layer 4 may be AlGaAs. The semiconductor quantum structure layer 3 and the uppermost semiconductor quantum dot layer 5 may be made of the same material as GaAs or different materials. In this specification, the above materials are mentioned as examples but the present disclosure is not limited thereto.

In a case where the semiconductor quantum structure layer 3 and the semiconductor quantum dot layer 5 are made of the same material and the same structure, the number of kinds of required materials is reduced, which allows simplified growth in the molecular beam epitaxy (MBE) equipment. In addition, since the same growth conditions may be applied for the growth of the semiconductor quantum structure layer 3 and the semiconductor quantum dot layer 5, surface density and size of the quantum dots of both layers may be adjusted more consistently.

By using the MBE equipment, a semiconductor specimen presenting a cross-sectional structure as shown in FIGS. 1A to 1D may be grown.

The semiconductor quantum dot may be formed by means of droplet epitaxy by using MBE equipment. The droplet epitaxy allows higher degree of controllability in size and surface density of quantum dots compared to the conventional Stranski-Krastanov (S-K) growth method, since the droplet epitaxy utilizes phase difference between different materials while the S-K method utilizes lattice constant mismatch between different materials. In the droplet epitaxy method, for example, in a case where GaAs is used as a material of the semiconductor quantum dots, the size and surface density of GaAs quantum dots may be controlled more easily by adjusting the size and surface density of Ga quantum dots. In detail, during the growth of a specimen including GaAs quantum dots, the Ga quantum dots are grown at first while the size and surface density of the Ga quantum dots may be determined by adjusting the amount of Ga injected and the temperature of the substrate is After the formation of the Ga quantum dots, the GaAs quantum dots may be formed by injecting As onto the Ga quantum dots so that the GaAs quantum dots become to have substantially the same size and surface density as the Ga quantum dots.

Any one or both of the semiconductor quantum dot layers, the uppermost layer (the semiconductor quantum dot layer 5) and the intermediate layer (the semiconductor quantum structure layer 3), may be formed by means of the droplet epitaxy (for example, GaAs quantum dots) as described above. Since the intermediate layer and the uppermost layer are independent from each other, the size and surface density of the quantum dots may be changed to meet the requirements of each layer.

In the droplet epitaxy method used in an embodiment, the size and surface density of the GaAs quantum dots may be controlled freely in a broader range in comparison to the S-K growth method by adjusting the size and surface density of the Ga quantum dots. In particular, the droplet epitaxy method is useful for low-density growth where the number of quantum dots per unit area is very small. In detail, when etching is performed on a specimen by using the aggregated materials as a mask, a single quantum dot may remain in each nano-structure only if the specimen includes a quantum dot layer of low surface density. For example, while the conventional S-K growth method gives a surface density of 200 to 300 $\mu m^{-2}$, the droplet epitaxy method may allow 10 to 50 $\mu m^{-2}$.

In an embodiment of the present disclosure, the specimen of FIG. 1D may be thermally treated in order to form aggregated materials which can be utilized as a mask. The thermal treatment may be performed by using a rapid thermal annealing (RTA) device. Accordingly, as shown in FIG. 1E, quantum dots in the uppermost layer are aggregated, and there is a statistical distribution in size so that large aggregated materials and small aggregated materials may be generated together. In an embodiment, it has been found that about 20 GaAs quantum dots are gathered to form one large aggregated material. In the RTA device, in order to minimize the damage of a specimen caused by evaporation of As element at high temperature, GaAs substrates may be used as protective layers. In detail, heating may be performed in a state where two impurity-undoped semi insulating GaAs substrates block both top and bottom surfaces of the specimen.

According to an embodiment, the thermal treatment may be performed for 30 seconds to 10 minutes at 500° C. to 1200° C. In an exemplary experiment, the thermal treatment is performed at 750° C. for 4 minutes.

In an embodiment of the present disclosure, in order to generate nano-structures, the specimen of FIG. 1E may be etched by using the uppermost aggregated GaAs 5'. At this stage, dry etching or wet etching may be used, and the present disclosure is not limited to a certain etching method.

In an embodiment, since the etch rate of AlGaAs (2, 4) and the etch rate of GaAs (3, 5') are substantially identical to each other in wet etching, structures shaped similar to the aggregated materials may be obtained after etching. Moreover, since the aggregated materials used as a mask for etching are entirely removed during the etching process, an additional process for removing the aggregated materials is not required after etching.

In addition, an etching depth may be determined in consideration of the height of the aggregated materials and the height from the bottom of the first semiconductor composite layer to the top of the second semiconductor composite layer, and the etching stage may be performed until the substrate is merely exposed (FIG. 1F), or partially etched (FIG. 1G).

In an exemplary experiment, an etchant based on sulfuric acid ($H_2SO_4:H_2O_2$:deionized water=1:8:40) is used in the wet etching process, and the wet etching is performed at the room temperature with an etch rate of about 10 nm per second.

Figure 3A:
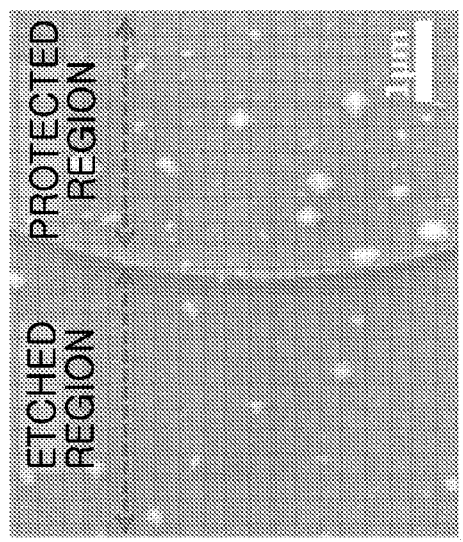
FIG. 3A-3B comparatively show nano-structures formed by performing the etching process according to an embodiment of the present invention (FIG. 3A) (an etched region) and aggregated materials formed on top of a specimen protected by E-beam resist (ER) to maintain the state before etching (a protected region) (FIG. 3B).
Figure 3B:
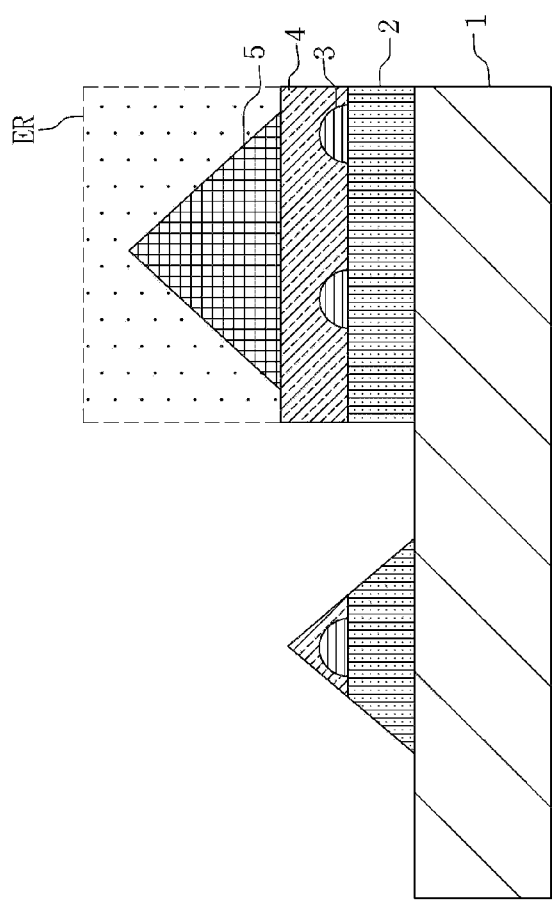

Referring to FIG. 3A-3B, a region including nano-structures where an etching process is performed according to an embodiment of the present disclosure (an etched region) and a region protected by E-beam resist (ER) to maintain the state before etching (a protected region) are comparatively shown.

FIG. 3A shows a nano-structure including only a single quantum dot etched by using an aggregated material as a mask according to an embodiment of the present disclosure. In addition, a cross-sectional view of the specimen shows an etched region and a protected region comparatively.

FIG. 3B shows a scanning electron microscopy (SEM) image of a specimen after etching, where brighter portions in the etched region correspond to nano-structures formed at the place where the semiconductor aggregated materials were positioned. In the protected region, where ER is removed for clear observation, small aggregated materials are distributed around large aggregated materials. However, it could be found that only the aggregated materials of a certain size or greater serve as a mask since all the aggregated materials of a certain size or smaller are removed during the etching process.

Figure 4A:
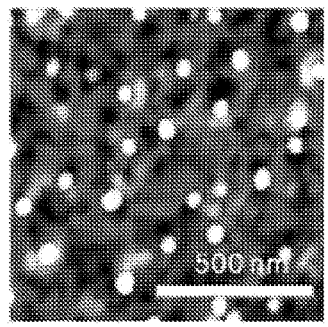
FIG. 4A-4B shows atomic force microscopy (AFM) images before (FIG. 4A) and after (FIG. 4B) the thermal treatment of quantum dots of a specimen according to an embodiment of the present disclosure.
Figure 4B:
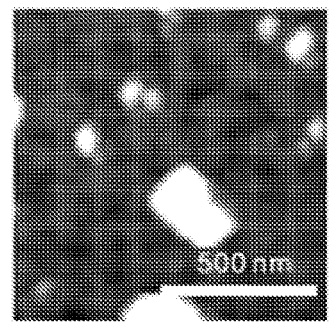

In an embodiment of the present disclosure, aggregated materials may be generated by thermal treatment of semiconductor quantum dots. In an embodiment, with a specimen heated at 750° C. for 4 minutes within high-purity nitrogen atmosphere, it is found that GaAs quantum dots are aggregated at the surface of the uppermost layer exposed outward so that aggregated materials are generated. Referring to FIG. 4A-4B showing an atomic force microscopy (AFM) images, before the thermal treatment (FIG. 4A), the quantum dots have an average diameter of about 50 nm, a height of about 15 nm, and a surface density of about 30 $\mu m^{-2}$. However, after the thermal treatment (FIG. 4B), the aggregated materials made of gathered quantum dots have an average diameter of about 300 nm, a height of about 100 nm, and a surface density of about 1.3 $\mu m^{-2}$ which is substantially reduced compared to the surface density of the quantum dots.

Additionally, in order to verify whether the size and surface density of the semiconductor aggregated materials may be controlled, specimens with quantum dots at the uppermost layer have different average sizes and surface densities are thermally treated. The result is shown as AFM images in FIG. 5.

Figure 5A:
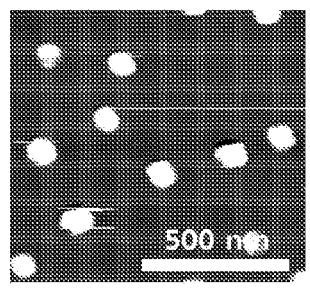
FIG. 5A-5B shows AFM images before (FIG. 5A) and after (FIG. 5B) the thermal treatment of another specimen where quantum dots at the uppermost layer have different average size and surface density compared to the specimen of FIG. 4.

As shown in FIG. 5A, before the thermal treatment, the quantum dots have an average diameter of about 100 nm, a height of about 30 nm, and a surface density of about 12 $\mu m^{-2}$. In this case, the average size is larger and the surface density is lower in comparison to the quantum dots of the specimen shown in FIG. 4. After the thermal treatment, as shown in FIG. 5B, the aggregated materials are formed to have an average diameter of about 130 nm, a height of about 50 nm, and a surface density of about 1 $\mu m^{-2}$.

Figure 5B:
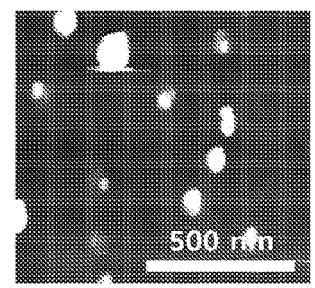

In the image of FIG. 5B, the aggregated materials appeared as brighter portions except one large aggregated material at the left top have an average height less than 10 nm so that may be removed during the following etching process. From the observation of the specimens shown in FIG. 4 and FIG. 5, it could be understood that the formation of the semiconductor aggregated materials may be controlled by changing the initial conditions of quantum dot growth as necessary, and the shape of the nano-structures may also be controlled as desired.

Figure 6A:
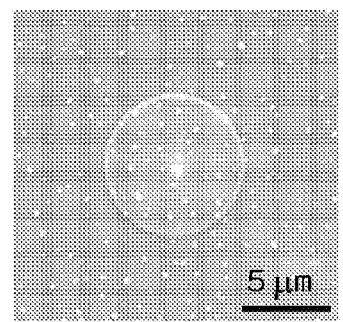
FIG. 6A-6B shows a scanning electron microscopy (SEM) image (FIG. 6A) and a cathodo-luminescence (CL) image (FIG. 6B) to demonstrate formation of nano-structures according to an embodiment of the present disclosure.
Figure 6B:
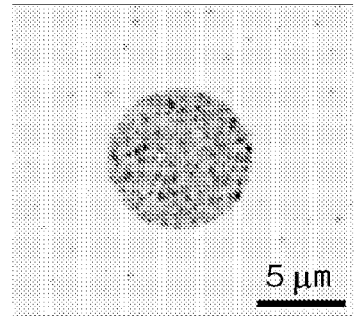

The images of FIG. 6A-6B demonstrate the formation of the nano-structures by an embodiment of the present disclosure. In the SEM image of FIG. 6A, the circle with a diameter of about 8 μm is the border where the inside is a protected region and the outside is an etched region. FIG. 6B shows a cathodo-luminescence (CL) measurement result at the same position as FIG. 6A. Since only the positions where light of a certain wavelength is emitted can be displayed darker in the CL measurement result image, if being measured tuned to the wavelength of light emitted from the quantum dots, the positions of the quantum dots are appeared as dark-colored dots and could be found clearly. As shown in FIG. 6B, in the etched region, quantum dots are present only in the positions where the semiconductor aggregated materials were once positioned so that quantum dots have a lower surface density compared to the protected region where quantum dots are distributed with a high surface density.

This is because the semiconductor aggregated materials served as a mask in the etching process to prevent the quantum dots at the intermediate layer from being etched and removed.

Figure 7:
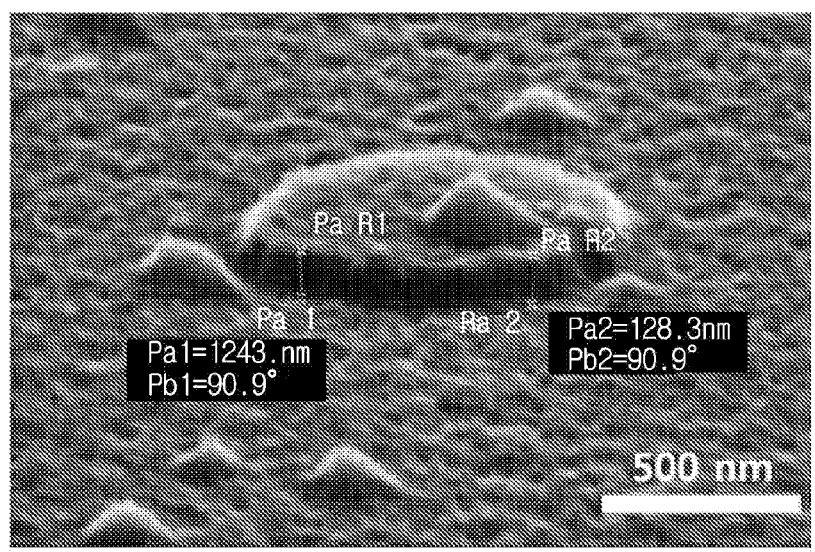
FIG. 7 shows an inclined-view SEM image for the same structure as FIG. 6A.

FIG. 7 shows an inclined-view SEM image having the same structure as FIG. 6A. Referring to FIG. 7, the semiconductor aggregated materials of the protected region and the nano-structures of the etched region have similar shapes, but only the nano-structures of the etched region include single quantum dots therein. Only when an etchant etches all the layers with the same etch rate, after the etching, nano-structures can be formed maintaining the initial shape of the semiconductor aggregated materials. Therefore, it is more advantageous if the semiconductor aggregated materials and the other layers have much more similar etch rates. However, in a case where the etch rate of each layer may be controlled and determined, more than one kind of etchant may be used to achieve the same result.

According to an embodiment of the present disclosure, when growing a specimen with a layer of compound semiconductor quantum dots, an additional layer of quantum dot may be further grown as the uppermost layer, and then the quantum dots at the uppermost layer become aggregated materials through suitable thermal treatment and used as a sacrificial mask to perform etching. This allows rapid manufacturing of nano-structures having desired average size and surface density on the entire surface of the specimen. Therefore, the surface density of the semiconductor quantum dots may be further lowered as necessary.

While the exemplary embodiments have been shown and described, it will be understood by those skilled in the art that various changes in form and details may be made thereto without departing from the spirit and scope of the present disclosure as defined by the appended claims. In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A nano-structure manufacturing method, comprising:
    forming a first semiconductor composite layer, a semiconductor quantum structure layer, a second semiconductor composite layer, and a semiconductor quantum dot layer on a substrate in order;
    thermally treating the semiconductor quantum dot layer so that quantum dots of the semiconductor quantum dot layer are aggregated; and
    performing an etching process by using the aggregated quantum dots as a mask, wherein the aggregated quantum dots used as the mask are entirely removed during the etching process; and
    obtaining structures shaped similar to the aggregated quantum dots after etching.

2. The nano-structure manufacturing method according to claim 1, wherein the semiconductor quantum structure layer includes at least one of a quantum dot, a quantum wire, a quantum well, a quantum dash, and a quantum molecule.

3. The nano-structure manufacturing method according to claim 1, wherein the quantum dots of the semiconductor quantum structure layer and the semiconductor quantum dot layer are made of the same semiconductor material.

4. The nano-structure manufacturing method according to claim 1, wherein the first semiconductor composite layer, the semiconductor quantum structure layer, the second semiconductor composite layer, and the semiconductor quantum dot layer are made of materials with the same etch rate.

5. The nano-structure manufacturing method according to claim 1, wherein the quantum dots of the semiconductor quantum structure layer and the semiconductor quantum dot layer are formed by means of droplet epitaxy.

6. The nano-structure manufacturing method according to claim 1, wherein the thermal treatment of the semiconductor quantum dot layer is performed by rapid thermal annealing at 500° C. to 1200° C. for 30 seconds to 10 minutes.

7. The nano-structure manufacturing method according to claim 6, wherein the thermal treatment of the semiconductor quantum dot layer includes:
    blocking both top and bottom surfaces of a specimen by using two impurity-undoped semi insulating (SI)-GaAs substrates; and
    performing thermal treatment at 750° C. for 4 minutes within nitrogen atmosphere.

8. The nano-structure manufacturing method according to claim 1, wherein the region from the bottom of the first semiconductor composite layer to the top of the second semiconductor composite layer is formed in the shape of the aggregated materials of the semiconductor quantum dot layer during the etching process utilizing the aggregated materials as a mask.

9. The nano-structure manufacturing method according to claim 3, wherein the quantum dots of the semiconductor quantum structure layer and the quantum dots of the semiconductor quantum dot layer are made of GaAs.

10. The nano-structure manufacturing method according to claim 9, wherein the first semiconductor composite layer and the second semiconductor composite layer are made of AlGaAs.

11. The nano-structure manufacturing method according to claim 9, wherein the GaAs quantum dots are formed by means of droplet epitaxy.

* * * * *